(12) United States Patent
Eun

(10) Patent No.: US 11,980,261 B2
(45) Date of Patent: May 14, 2024

(54) ORNAMENT CAPABLE OF ADJUSTING AMOUNT OF EMITTED FRAGRANCE

(71) Applicant: CERAART CO., LTD., Seongnam-si (KR)

(72) Inventor: Kyoung A Eun, Gwangju-si (KR)

(73) Assignee: CERAART CO., LTD., Seongnam-si (KR)

( * ) Notice: Subject to any disclaimer, the term of this patent is extended or adjusted under 35 U.S.C. 154(b) by 554 days.

(21) Appl. No.: 17/284,655

(22) PCT Filed: Jul. 17, 2019

(86) PCT No.: PCT/KR2019/008854
§ 371 (c)(1),
(2) Date: Apr. 12, 2021

(87) PCT Pub. No.: WO2020/080649
PCT Pub. Date: Apr. 23, 2020

(65) Prior Publication Data
US 2021/0393005 A1  Dec. 23, 2021

(30) Foreign Application Priority Data

Oct. 16, 2018 (KR) .................. 10-2018-0123134
Mar. 6, 2019 (KR) .................. 10-2019-0026001
Mar. 6, 2019 (KR) .................. 20-2019-0000932

(51) Int. Cl.
*A44C 15/00* (2006.01)
*A61L 9/03* (2006.01)

(52) U.S. Cl.
CPC .............. *A44C 15/002* (2013.01); *A61L 9/03* (2013.01); *A61L 2209/133* (2013.01); *A61L 2209/134* (2013.01)

(58) Field of Classification Search
CPC ... A44C 15/002; A61L 9/03; A61L 2209/133; A61L 2209/134
(Continued)

(56) References Cited

U.S. PATENT DOCUMENTS 5,299,736 A * 4/1994 Greene .................. A61L 9/12
239/34
6,367,706 B1 4/2002 Putz
(Continued)

FOREIGN PATENT DOCUMENTS

JP     06029547     4/1994
JP     3000181      8/1994
(Continued)

OTHER PUBLICATIONS

International Search Report—PCT/KR2019/008854 dated Oct. 29, 2019.

*Primary Examiner* — Steven J Ganey
(74) *Attorney, Agent, or Firm* — CANTOR COLBURN LLP

(57) ABSTRACT

Provided is an ornament adjustable in amount of fragrance emitted therefrom that is capable of providing aesthetic beauty when worn on the human body, while having a function of emitting fragrance, thereby helping the stability of the wearer through an olfactory stimulus and expressing the wearer's uniqueness from the people around him or her, that is capable of exchanging the fragrance with new one easily and conveniently according to the wearer's fragrance preference, and that is capable of allowing the amount of fragrance emitted from a fragrance cartridge accommodated therein to be easily and simply adjusted through various modes according to the wearer's preference or wearing
(Continued)

environments, thereby extending the use time of the fragrance cartridge and ensuring luxury and sensible fragrance coordination.

20 Claims, 10 Drawing Sheets

(58) Field of Classification Search
USPC .................................. 239/34, 36, 53, 55, 57
See application file for complete search history.

(56) References Cited

U.S. PATENT DOCUMENTS

| | | | |
|---|---|---|---|
| 8,919,662 B2* | 12/2014 | Sherwood | A61L 9/12 |
| | | | 239/54 |
| 2007/0234757 A1 | 10/2007 | Sherman | |
| 2016/0114070 A1* | 4/2016 | Atkinson | A61L 9/127 |
| | | | 239/34 |

FOREIGN PATENT DOCUMENTS

| | | |
|---|---|---|
| JP | 3108423 | 4/2005 |
| JP | 3188540 | 1/2014 |
| KR | 200323056 | 8/2003 |
| KR | 200359069 | 8/2004 |
| KR | 200470374 | 12/2013 |
| KR | 20140086891 | 7/2014 |
| WO | 2018011780 | 1/2018 |

* cited by examiner (a)

(b)

(a)

(b)

ORNAMENT CAPABLE OF ADJUSTING AMOUNT OF EMITTED FRAGRANCE

TECHNICAL FIELD

The present invention relates to an ornament adjustable in amount of fragrance emitted therefrom, and more particularly, to an ornament adjustable in amount of fragrance emitted therefrom that is capable of providing aesthetic beauty when worn on the human body, while having a function of emitting fragrance, thereby helping the stability of the wearer through an olfactory stimulus and expressing the wearer's uniqueness from the people around him or her, that is capable of exchanging the fragrance with new one easily and conveniently according to the wearer's fragrance preference, that is capable of allowing the amount of fragrance emitted from a fragrance cartridge accommodated therein to be easily and simply adjusted through various modes according to the wearer's preference or wearing environments, thereby extending the use time of the fragrance cartridge and ensuring luxury and sensible fragrance coordination, and that is capable of emitting an abundant amount of fragrance while being worn on the wearer, whereas emitting an extremely small amount of fragrance while being not worn on the wearer, thereby saving the amount of fragrance emitted from the fragrance cartridge and enabling the sensible utilization thereof.

BACKGROUND ART

Generally, an ornament is worn on the human body to provide the wearer's aesthetic beauty and simultaneously to express his or her uniqueness. Recently, functional ornament products, in which a fragrance or air freshener is built to thus provide a fragrance emission function, have been launched to the market.

If most of the functional ornament products in which the fragrance or air freshener is accommodated consume their fragrance emitted therefrom, however, their function as the fragrance becomes lost. Accordingly, if the ornament is purchased for the purpose of the fragrance, the use purpose of the ornament is lost due to all the emission of the fragrance, even while the ornament is not used for a long time. The wearer does not have any attraction and interest in wearing the ornament anymore, which undesirably causes the life span of the ornament to be substantially short.

In a process of using the ornament product, not in a process of manufacturing the ornament product, further, it is very hard to build the fragrance or air freshener in the ornament, and it is inconvenient to exchange the fragrance or air freshener with new one. Since the existing fragrance or air freshener has a short period of use, also, it should be frequently exchanged, and otherwise, the fragrance has to be put in the ornament periodically.

Up to now, further, the fragrance emitting ornament has been made by applying an air freshener or additive onto the surface thereof or attaching separate solid fragrance to the underside thereof. In the same manner as above, however, the fragrance is all emitted and consumed after used for a given period of time, and accordingly, the ornament is used just one time.

If the wearer has an allergic reaction with a fragrance emitting substance, he or she is reluctant to come into direct contact with the fragrance emitting substance, but since most of ornaments are provided by applying fragrance onto the surfaces thereof or by exposing the fragrance emitting substance to the outer surfaces thereof, the skin of the wearer may be damaged seriously due to the allergic reaction.

On the other hand, in the case of the existing ornament product in which the fragrance or air freshener is built, the air freshener has the amount of fragrance emitted limited to a given period of time, and even while the ornament product is not used or worn, the given amount of fragrance emitted is kept, thereby causing unnecessary fragrance emission. As a result, the use time of the air freshener in the ornament is reduced to make a degree of preference for the ornament product with the air freshener built therein lowered. Moreover, the ornament is generally worn when the wearer goes out, but there is a need to adjust the amount of fragrance emitted according to the fragrance preference of the other person or the characteristics of the wearing environment. Up to now, however, the ornament product with the air freshener built therein is impossible in adjusting the amount of fragrance emitted therefrom, and even though the amount of fragrance emitted is adjustable, the adjustment is not easy and convenient.

In addition, the ornament is used while worn on the wearer and is kept while not worn on him or her. The fragrance emitting ornament has a given amount of fragrance emitted therefrom, and if a large amount of fragrance is emitted, while the ornament is kept at a given place, without being worn on the wearer, the raw fragrance liquid in the ornament may be rapidly consumed, thereby making the use effectiveness of the fragrance emitting ornament deteriorated. In specific, in the case of the ornament like a bracelet or earring, the time during which the ornament is kept at a given place is longer than the time during which the ornament is really worn on the wearer, and accordingly, the wearer doubts whether the fragrance emitting ornament is effective.

DISCLOSURE

Technical Problem

Accordingly, the present invention has been made in view of the above-mentioned problems occurring in the related art, and it is an object of the present invention to provide an ornament adjustable in amount of fragrance emitted therefrom that is capable of providing aesthetic beauty when worn on the human body, while having a function of emitting fragrance, thereby helping the stability of the wearer through an olfactory stimulus and expressing the wearer's uniqueness from the people around him or her, and that is capable of exchanging the fragrance with new one easily and conveniently according to the wearer's fragrance preference.

It is another object of the present invention to provide an ornament adjustable in amount of fragrance emitted therefrom that is capable of allowing the amount of fragrance emitted from a fragrance cartridge accommodated therein to be easily and simply adjusted through various modes according to a wearer's preference or wearing environments, thereby extending the use time of the fragrance cartridge and ensuring luxury and sensible fragrance coordination.

It is yet another object of the present invention to provide an ornament adjustable in amount of fragrance emitted therefrom that is capable of allowing the amount of fragrance emitted from a fragrance cartridge accommodated therein to be easily and simply adjusted through various modes according to a wearer's preference or wearing environments, thereby extending the use time of the fragrance cartridge and ensuring luxury and sensible fragrance coordination.

It is still another object of the present invention to provide an ornament adjustable in amount of fragrance emitted therefrom that is capable of emitting an abundant amount of fragrance when worn on a wearer, while emitting an extremely small amount of fragrance while being not worn on the wearer, thereby saving the amount of fragrance emitted from a fragrance cartridge and enabling the sensible utilization thereof.

Technical Solution

To accomplish the above-mentioned objects, according to one aspect of the present invention, there is provided an ornament including: a body having an accommodation space formed therein; and a fragrance cartridge accommodatedly located in the accommodation space of the body and having internal pores adapted to contain a raw fragrance liquid therein, wherein the body and the fragrance cartridge are made of a ceramic material.

Desirably, the body has the shape of a main ornamental part of any one selected from various ornaments such as a bracelet, pendant, ring, earring, necklace, anklet, brooch, hair band, hair pin, medal, clip, and so on, and otherwise, the body has the shape of an auxiliary ornamental part adapted to allow the main ornamental part to be worn on the human body.

Desirably, the body has any one of zirconia ($ZrO_2$) and alumina ($Al_2O_3$) as a main material so that the body becomes the ceramic material.

Desirably, the fragrance cartridge has any one of zirconia and alumina as a main material so that the fragrance cartridge becomes porous ceramic.

Desirably, the fragrance cartridge is submerged into the raw fragrance liquid or is sprayed or coated with the raw fragrance liquid so as to contain the raw fragrance liquid in the internal pores thereof.

Desirably, the body includes: a base adapted to accommodate the fragrance cartridge therein in such a manner as to allow one surface of the fragrance cartridge to be exposed to the outside; and a cover adapted to cover one surface of the base in such a manner as to allow an open state thereof to be changed by means of a wearer's finger motion.

Desirably, the base includes: an accommodation recess formed in the middle portion of top surface thereof to accommodate the fragrance cartridge thereinto; a hinge pin located on one side of top surface thereof around the accommodation recess; and a first coupling magnet and a second coupling magnet located on the bottom of the accommodation recess, and the cover includes a first sliding magnet and a second sliding magnet located on the corresponding positions facing the first coupling magnet and the second coupling magnet of the base, whereby the base and the cover are coupled to each other by means of the hinge pin to allow the cover to horizontally swing on the base.

Desirably, the first coupling magnet and the second coupling magnet of the base have the same polarities as each other, and the first sliding magnet and the second sliding magnet of the cover have the opposite polarities to the first coupling magnet and the second coupling magnet of the base.

Desirably, the first coupling magnet of the base is coupled to the first sliding magnet of the cover by means of magnetic forces thereof, and the second coupling magnet of the base is coupled to the second sliding magnet of the cover by means of magnetic forces thereof, so that the body emits fragrance in a closed mode with no exposure of the accommodation recess having the fragrance cartridge built therein to the outside.

Desirably, if the cover is pushed by the wearer and horizontally swings around the hinge pin, the first sliding magnet of the cover is moved in position and is thus coupled to the second coupling magnet of the base by means of the magnetic forces, with no coupling between the first coupling magnet of the base and the second sliding magnet of the cover, so that the body emits the fragrance in a wearer side quarter open mode in which a portion of the fragrance cartridge is exposed to the wearer side.

Desirably, a given arrangement is made to satisfy the following Mathematical equation so that the conversion into the wearer side quarter open mode is performed, $$L_{2b} - D_{2b} \leq L_{1c} \leq L_{2b} + D_{2b}$$ [Mathematical equation]

wherein the $L_{1c}$ indicates a distance from the hinge pin to the center of the first sliding magnet, the $L_{2b}$ indicates a distance from the hinge pin to the center of the second coupling magnet, and the $D_{2b}$ indicates an average distance from the center of the second coupling magnet to the outermost periphery thereof.

Desirably, a given arrangement is made to satisfy the following Mathematical equation so that the conversion into the wearer side quarter open mode is performed according to the rotation of the cover in one direction, $$|L_{1c} - L_{2b}| > D_{1c} + D_{2b}$$ [Mathematical equation]

wherein the $D_{1c}$ indicates an average distance from the center of the second sliding magnet to the outermost periphery thereof, and the $|L_{1c} - L_{2b}|$ indicates an absolute value of $L_{1c} - L_{2b}$.

Desirably, if the cover is pushed by the wearer and horizontally swings around the hinge pin, the second sliding magnet of the cover is moved in position and is thus coupled to the first coupling magnet of the base by means of the magnetic forces, with no coupling between the second coupling magnet of the base and the first sliding magnet of the cover, so that the body emits the fragrance in the other person side quarter open mode in which a portion of the fragrance cartridge is exposed to the other person side.

Desirably, a given arrangement is made to satisfy the following Mathematical equation so that the state conversion into the other person side quarter open mode is performed, $$L_{1b} - D_{1b} \leq L_{2c} \leq L_{1b} + D_{1b}$$ Mathematical equation]

wherein the $L_{2c}$ indicates a distance from the hinge pin to the center of the second sliding magnet, the $L_{1b}$ indicates a distance from the hinge pin to the center of the first coupling magnet, and the $D_{1b}$ indicates an average distance from the center of the first coupling magnet to the outermost periphery thereof.

Desirably, a given arrangement is made to satisfy the following Mathematical equation so that the conversion into the other person side quarter open mode is performed according to the rotation of the cover in one direction, while the cover is idling according to the rotation in the opposite direction to one direction, $$|L_{2c} - L_{1b}| > D_{2c} + D_{1b}$$ [Mathematical equation]

wherein the $D_{2c}$ indicates an average distance from the center of the second sliding magnet to the outermost periphery thereof, and the $|L_{2c} - L_{1b}|$ indicates an absolute value of $L_{2c} - L_{1b}$.

Desirably, if the cover is pushed by the wearer and horizontally swings around the hinge pin, no coupling occurs between the first coupling magnet and the second coupling magnet of the base and the first sliding magnet and the second sliding magnet of the cover, so that the body emits the fragrance in a half open mode in which a portion of the fragrance cartridge is exposed to the other person side.

Desirably, if the hinge pin is removed from the base and the cover to separate the cover from the base, the body emits the fragrance in a full open mode in which the fragrance cartridge is fully exposed to the outside.

To accomplish the above-mentioned objects, according to another aspect of the present invention, there is provided an ornament including: a body having an accommodation space formed therein and a contact wall located on the underside thereof to constitute the accommodation space, the contact wall coming into contact with the human body; and a fragrance cartridge accommodatedly located in the accommodation space of the body in such a manner as to face the contact wall, wherein the contact wall is made of a non-porous ceramic material, has a thickness of 1.5 to 2.9 mm, and the fragrance cartridge is made of a porous ceramic material, has a thickness of 0.5 to 1.3 mm, contains a raw fragrance liquid in internal pores thereof, and receives the body temperature of a wearer coming into direct contact with the contact wall to emit the fragrance contained therein.

Desirably, the body and the fragrance cartridge have any one of zirconia ($ZrO_2$) and alumina ($Al_2O_3$) as a main material so that the body and the fragrance cartridge become the ceramic material.

Desirably, the fragrance cartridge is submerged into the raw fragrance liquid or is sprayed or coated with the raw fragrance liquid so as to contain the raw fragrance liquid in the internal pores thereof.

Desirably, the body and the fragrance cartridge have zirconia as a main material so that the body and the fragrance cartridge become the ceramic material, the fragrance cartridge has the internal pore sizes of 10 to 200 μm and porosity of 10 to 70%, the contact wall has a thickness of 2.5 to 2.7 mm, and the fragrance cartridge has a thickness of 0.9 to 1.3 mm, so that the fragrance is emitted over a day and the amount of fragrance emitted is automatically adjusted according to whether the ornament is worn.

Advantageous Effects

According to the present invention, the ornament can provide the aesthetic beauty when worn on the human body, while having a function of emitting fragrance therefrom, thereby helping the stability of the wearer through the olfactory stimulus and expressing the wearer's uniqueness from the people around him or her.

In addition, the ornament according to the present invention can exchange the fragrance with new one easily and conveniently according to the wearer's fragrance preference, thereby enabling the semi-permanent use thereof.

Further, the ornament according to the present invention can prevent the fragrance cartridge for emitting fragrance from coming into direct contact with the skin, thereby being safely usable even by a wearer who has an allergic reaction with respect to a fragrance emitting substance.

Also, the ornament according to the present invention can allow the amount of fragrance emitted from the fragrance cartridge accommodated therein to be easily and simply adjusted through various modes according to the wearer's preference or wearing environments, thereby extending the use time of the fragrance cartridge and ensuring luxury and sensible fragrance coordination.

Moreover, the ornament according to the present invention can emit an abundant amount of fragrance when worn on the wearer, while emitting an extremely small amount of fragrance while being not worn on the wearer, thereby saving the amount of fragrance emitted from a fragrance cartridge and enabling the sensible utilization thereof.

MODE FOR INVENTION

Figure 1:
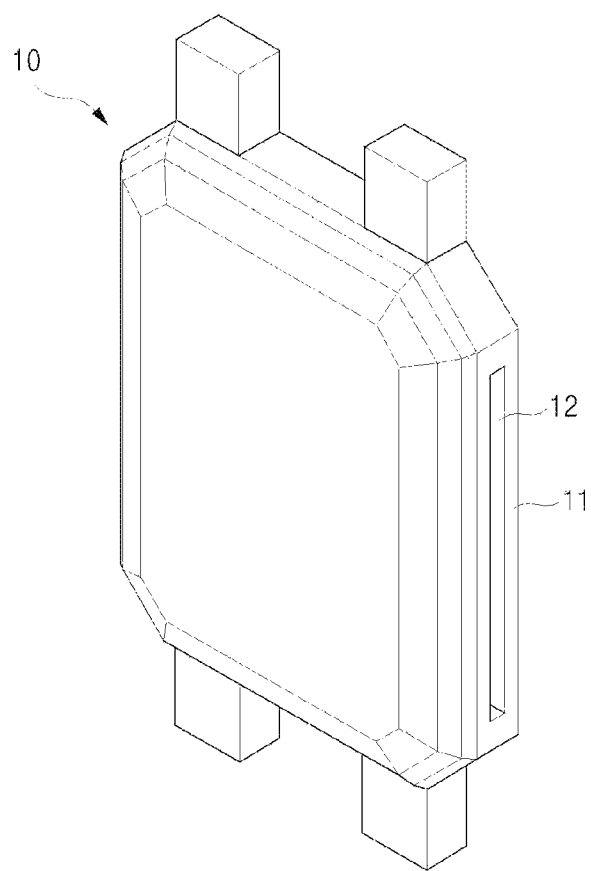
FIG. 1 is a perspective view showing a body of an ornament according to a first embodiment of the present invention.

Hereinafter, the present invention is disclosed with reference to the attached drawings wherein the corresponding parts in the embodiments of the present invention are indicated by corresponding reference numerals and the repeated explanation on the corresponding parts will be avoided. If it is determined that the detailed explanation on the well known technology related to the present invention makes the scope of the present invention not clear, the explanation will be avoided for the brevity of the description.

Figure 2:
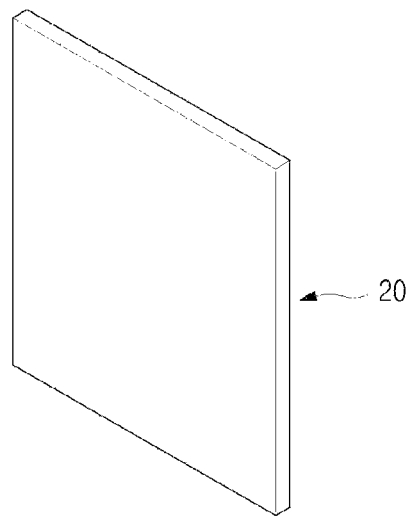
FIG. 2 is a perspective view showing a fragrance cartridge of the ornament according to the first embodiment of the present invention.

FIG. 1 is a perspective view showing a body of an ornament according to a first embodiment of the present invention, and FIG. 2 is a perspective view showing a fragrance cartridge of the ornament according to the first embodiment of the present invention.

Referring to FIGS. 1 and 2, a fragrance emitting ornament according to a first embodiment of the present invention includes a body 10 worn on the human body to provide aesthetic beauty and a fragrance cartridge 20 coupled to the body 10 to emit fragrance therefrom.

The body 10 as an ornament is worn on the human body to express aesthetic beauty from the outer appearance thereof.

The body 10 may have various shapes. For example, the body 10 has the shape of a main ornamental part for any one selected from various ornaments such as a bracelet, pendant, ring, earring, necklace, anklet, brooch, hair band, hair pin, medal, clip, and so on, and otherwise, the body 10 has the shape of an auxiliary ornamental part like a connector adapted to allow the main ornamental part to be worn on the human body. For example, the body 10 as shown in FIG. 1 is a bracelet head as the main ornamental part constituting the bracelet.

In specific, the body 10 is made of a ceramic material.

Generally, various ornaments, which are configured to impregnate fragrance or smell into a porous metal material to consistently emit the fragrance or smell therefrom, have been provided, but because of the use of the metal material, in this case, biocompatibility and feeling of wearing become deteriorated to cause a low degree of preference in market. Further, the specific gravity of the metal material is high, thereby having limitations in making the ornament to size and shape as required, and the strength or hardness of the metal material is low, thereby causing bad durability and productivity.

According to the present invention, the body 10 is made of the ceramic material, thereby enhancing the strength and hardness thereof, and accordingly, the ornament product has high rigidity so that it can be prevented from being damaged. Further, scratches, which may be generated during daily living, do not appear on the outer surface of the body 10 well, and a good gloss treatment is performed on the surface of the body 10, thereby advantageously ensuring high productivity.

The body 10 is made by uniformly mixing a raw ceramic material, filling the mixed ceramic material in a mold, and sintering the filled ceramic material at a high temperature. In this case, the raw ceramic material has zirconia ($ZrO_2$) or alumina ($Al_2O_3$) as a main material, and the molded product stabilized after the sintering step is subjected to gloss surface polishing by means of a diamond abrasive tool or to shape polishing to thus have the surface and shape close to a semi-precious jewel.

In this case, the body 10 has an accommodation portion 12 formed as an empty space in an interior thereof, and the accommodation portion 12 has a contact wall 11 serving as at least one outer surface defining the empty space. The contact wall 11 is located between the fragrance cartridge 20 in the accommodation portion 12 of the body 10 and a wearer's skin when the ornament is worn on the wearer.

The accommodation portion 12 is the space into which the fragrance cartridge 20 is inserted.

The contact wall 11 is one of the surfaces defining the space of the accommodation portion 12, particularly the surface coming into direct contact with the human body when the body 10 as the ornament is worn on the human body. The fragrance cartridge 20 contains a fragrance emitting substance in internal pores thereof so as to emit given fragrance therefrom, but if the wearer has an allergic reaction with respect to the fragrance emitting substance, his or her skin may be seriously damaged. So as to prevent the fragrance cartridge 20 inserted into the accommodation portion 12 from coming into direct contact with the skin, accordingly, the accommodation portion 12 has to have the contact wall 11.

In this case, desirably, the space shape of the accommodation portion 12 corresponds to the outer shape of the fragrance cartridge 20, and of course, the accommodation portion 12 may be changed in shape by means of a mechanism for maintaining the inserted state of the fragrance cartridge or a mechanism for inserting or drawing the fragrance cartridge 20.

Also, the body 10 has through holes (not shown) formed thereon to emit the fragrance emitted from the fragrance cartridge 20 built in the accommodation portion 12 to the outside thereof.

The fragrance cartridge 20 has the shape capable of being inserted into the accommodation portion 12 of the body 10 and provides a fragrance emitting function.

The fragrance cartridge 20 has various shapes, and only if the fragrance cartridge 20 is built in the accommodation portion 12 of the body, it is not particularly limited in shape. For example, the fragrance cartridge 20 as shown in FIG. 2 has the shape of a square plate.

In specific, the fragrance cartridge 20 is made of a ceramic material. The fragrance cartridge 20 is made by selecting any one of zirconia ($ZrO_2$) and alumina ($Al_2O_3$) as a main material, filling the selected material in a mold, pressurizing the filled material under a given pressure to make pores thereon, and sintering the molded material at a high temperature. Accordingly, the pores of the fragrance cartridge 20 made of the ceramic material contain the fragrance emitting substance.

If the fragrance cartridge 20 with the pores formed thereon is submerged into a raw fragrance liquid for given time, the raw fragrance liquid is contained in the pores of the fragrance cartridge 20 by means of capillary action, and as the raw fragrance liquid contained in the pores of the fragrance cartridge 20 is emitted slowly from the pores to the outside, fragrance emission is carried out.

In this case, an example in which the fragrance cartridge 20 with the pores formed thereon is submerged into the raw fragrance liquid for the given time has been explained above, but so as to allow the raw fragrance liquid to be contained in the pores of the fragrance cartridge 20, in addition thereto, the raw fragrance liquid may be sprayed or applied onto the fragrance cartridge 20.

Like this, the fragrance cartridge 20 with the fragrance contained therein is built in the body 10 having aesthetic beauty and is thus kept therein by means of various methods.

Figure 3:
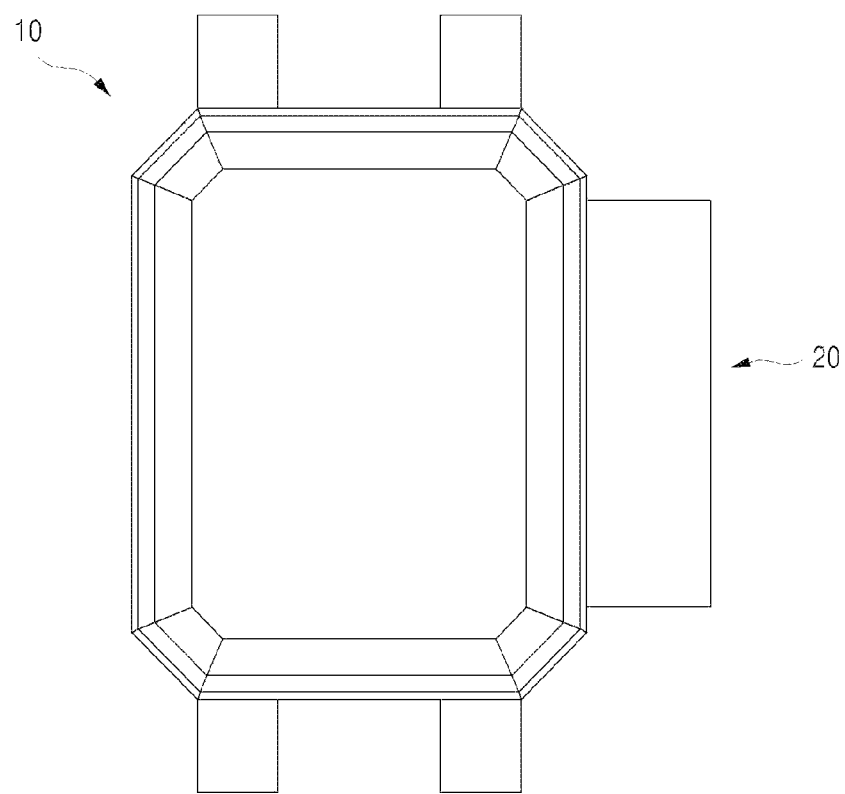
FIG. 3 is a front view showing a coupling process between the body and the fragrance cartridge of the ornament according to the first embodiment of the present invention.

First, FIG. 3 shows a process of coupling and separating the fragrance cartridge 20 to and from the body 10 by means of a drawer type coupling method.

The fragrance cartridge 20 has the shape of a flat plate, and the accommodation portion 12 of the body 10 is formed as a plate-shaped empty space in which the fragrance cartridge 20 can be built. In this case, the accommodation portion 12 has an inlet exposed to the outside to push and draw the fragrance cartridge 20 thereinto and therefrom. Accordingly, the wearer can exchange the fragrance cartridge 20 easily and conveniently only by means of simple operations like pushing and drawing the fragrance cartridge 20, so that the wearer can freely select his or her desired fragrance according to his or her fragrance preference.

In this case, the accommodation portion 12 of the body has an accommodation support (not shown) adapted to support the fragrance cartridge 20 built therein to thus prevent the fragrance cartridge 20 from easily escaping therefrom.

Figure 4:
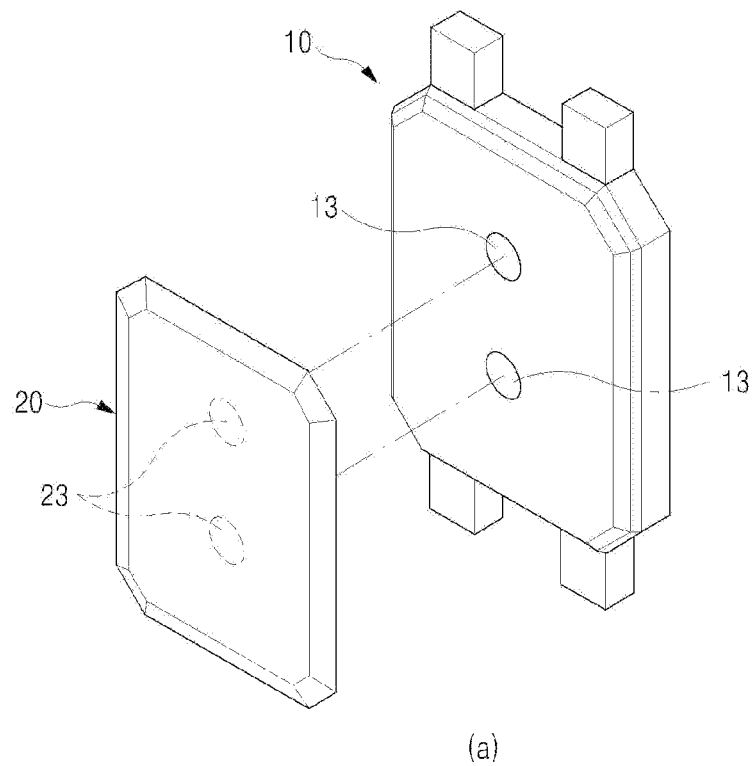
FIG. 4 is perspective views showing another example of the coupling process between the body and the fragrance cartridge of the ornament according to the first embodiment of the present invention.
Figure 4:
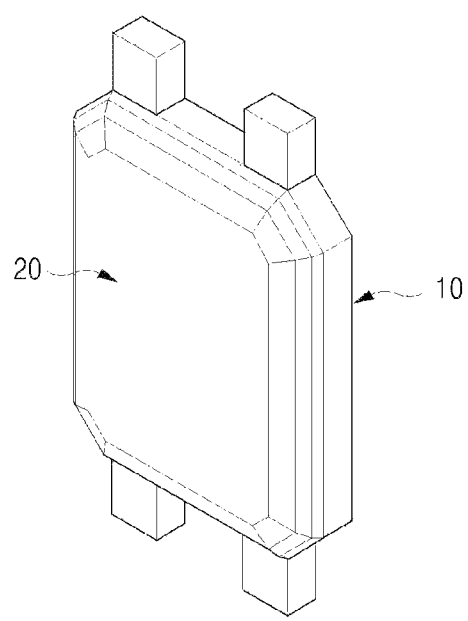

Next, FIGS. 4A and 4B show another coupling process between the body 10 and the fragrance cartridge 20.

FIGS. 4A and 4B are perspective views showing another example of the coupling process between the body 10 and the fragrance cartridge 20 of the ornament according to the first embodiment of the present invention.

Referring to FIGS. 4A and 4B, the body 10 has coupling magnets 13 located on a coupling surface exposed to the outside. Further, the fragrance cartridge 20 has coupling magnets 23 located on a coupling surface coming into contact with the coupling surface of the body 10 in such a manner as to correspond to the coupling magnets 13 of the body 10.

Through the coupling magnets 13 and 23, accordingly, the fragrance cartridge 20 can be coupled to the outer surface of the body 10. As shown in FIGS. 4A and 4B, the outer shape of the fragrance cartridge 20 corresponds to that of the body 10, and when the fragrance cartridge 20 is coupled to the body 10, accordingly, they can be seen as one ornament, thereby more enhancing the aesthetic beauty of the ornament.

In this case, the coupling magnets 13 of the body 10 have different polarities from the coupling magnets 23 of the fragrance cartridge 20 so as to achieve their coupling, and it is possible that either the coupling magnets 13 of the body 10 or the coupling magnets 23 of the fragrance cartridge 20 may be made of a metal material.

Now, an explanation of an ornament according to a second embodiment of the present invention will be in detail given with reference to FIGS. 5 to 11.

Figure 5:
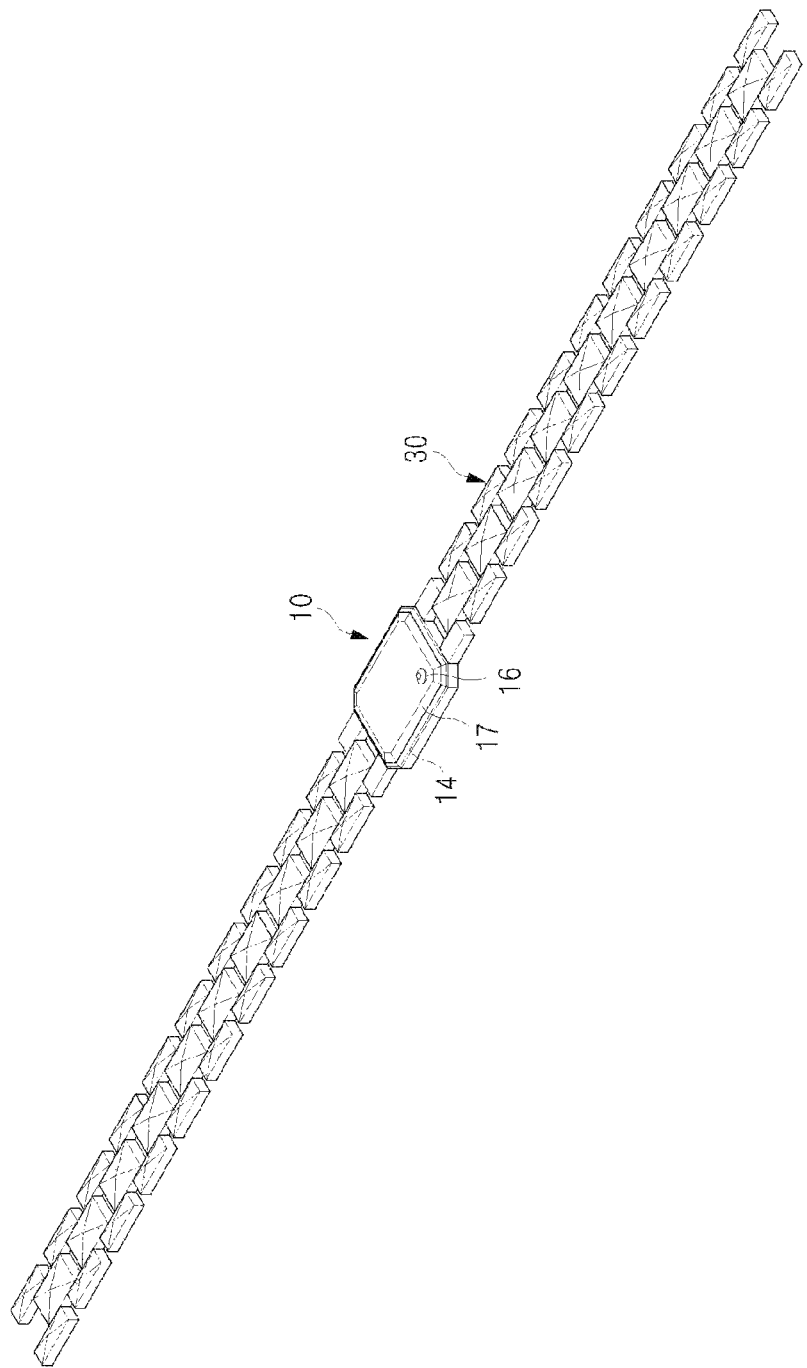
FIG. 5 is a perspective view showing an ornament according to a second embodiment of the present invention.

FIG. 5 is a perspective view showing an ornament according to a second embodiment of the present invention.

As shown in FIG. 5, the ornament according to the second embodiment of the present invention is applied to a head portion of a bracelet, and while the bracelet is worn on a user, fragrance is gently emitted from the head portion of the bracelet around the wearer, thereby expressing the wearer's uniqueness and attraction.

In this case, the wearer becomes in various situations in which he or she meets many people and joins in different kinds of meetings. In specific, the wearer wants to appeal his or her attraction through relatively strong fragrance when he or she meets someone, and contrarily, he or she wants to avoid his or her existence from standing out through relatively soft fragrance when he or she joins in a given meeting.

However, the ornament according to the first embodiment of the present invention just has the fragrance emission outlet (that is, the inlet exposed to the outside to push and draw the fragrance cartridge 20) fixed in size, and accordingly, an amount of fragrance emitted cannot be freely adjusted according to the wearer's preference or wearing environment. Of course, a door may be additionally provided simply to open and close the fragrance emission outlet, but according to the characteristics of the material (ceramic), it is not easy to install the door. Through the addition of the door, besides, it is difficult to expect various fragrance emission modes in which desired amounts of fragrance emitted can be determined according to the wearer's situations.

So as to overcome the problems, as shown in FIG. 5, a body 10 of the ornament according to the second embodiment of the present invention includes a base 14 adapted to accommodate a fragrance cartridge 20 therein in such a manner as to allow one surface of the fragrance cartridge 20 to be exposed to the outside and a cover 17 adapted to cover one surface of the base 14 in such a manner as to allow a degree of openness thereof to be changed by means of a wearer's simple finger motion. The body 10 as a main ornamental part constituting a bracelet has both ends fastened to straps 30.

Figure 6:
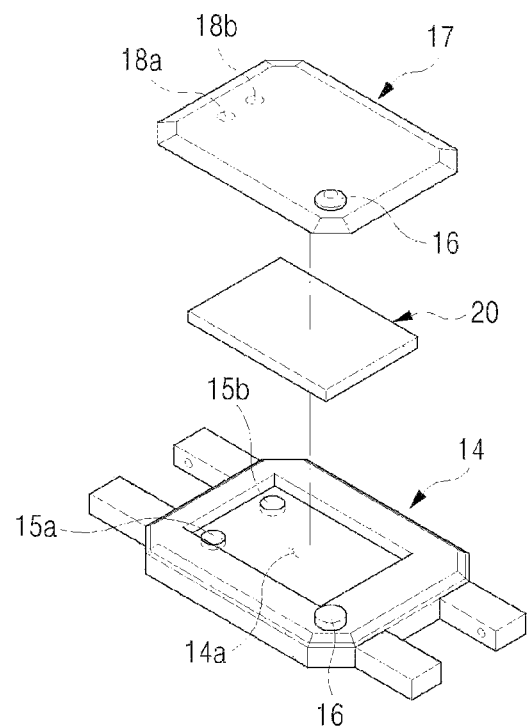
FIG. 6 is an exploded perspective view showing a body of the ornament according to the second embodiment of the present invention.

Referring to FIG. 6, the base 14 has an accommodation recess 14a formed in the middle portion of top surface thereof to accommodate the fragrance cartridge 20 thereinto. A depth of the accommodation recess 14a is equal to or greater than a thickness of the fragrance cartridge 20, so that swing motions of the cover 17 as will be discussed later cannot be limited by means of the fragrance cartridge 20.

Further, the base 14 is the surface coming into direct contact with the human body when the body 10 as the ornament is worn on the human body. The fragrance cartridge 20 contains a fragrance emitting substance in internal pores thereof so as to emit given fragrance therefrom, but if the wearer has an allergic reaction with the fragrance emitting substance, his or her skin may be seriously damaged. So as to prevent the fragrance cartridge 20 from coming into direct contact with the skin, accordingly, the body 10 has to have the base 14.

Further, the body 10 has a hinge pin 16 located on one side of top surface of the base 14 around the accommodation recess 14a in such a manner as to be coupled to the cover 17, and through the hinge pin 16, the base 14 and the cover 17 can be coupled to each other. Accordingly, the cover 17 can swing horizontally on the base 14 around the hinge pin 16. So as to allow the cover 17 to rotate with respect to the base 14, as shown, the hinge pin 16 is rotatably coupled to the cover 17, and the body of the hinge pin 16 is inserted into the base 14. Unlike this, pins may be rotatably coupled to the cover 17 and the base 14, respectively, and the ends of the pins may be inserted into one tube.

Further, the body 10 has a first coupling magnet 15a and a second coupling magnet 15b located on the bottom of the accommodation recess 14a.

On the other hand, the cover 17 has a first sliding magnet 18a and a second sliding magnet 18b located on the corresponding positions facing the first coupling magnet 15a and the second coupling magnet 15b on the underside thereof. In this case, the first coupling magnet 15a and the second coupling magnet 15b of the base 14 are not exposed to the outside by means of the fragrance cartridge 20 when the base 14 is coupled to the fragrance cartridge 20.

Further, the first coupling magnet 15a and the second coupling magnet 15b of the base 14 have the same polarities as each other, and contrarily, the first sliding magnet 18a and the second sliding magnet 18b of the cover 17 have the opposite polarities to the first coupling magnet 15a and the second coupling magnet 15b of the base 14.

In accordance with the magnetic coupling states between the first coupling magnet 15a and the second coupling magnet 15b of the base 14 and the first sliding magnet 18a and the second sliding magnet 18b of the cover 17, the body 10 as the ornament according to the second embodiment of the present invention can operate in various fragrance emission modes.

FIGS. 7 to 11 are perspective views showing various fragrance emission modes of the ornament according to the second embodiment of the present invention.

Figure 7:
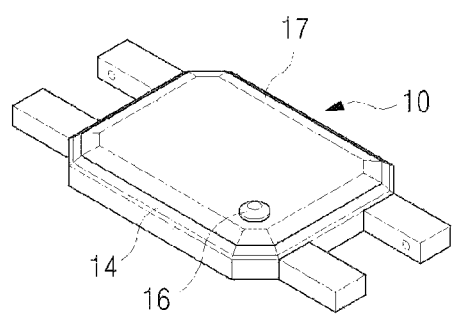
FIGS. 7 to 11 are perspective views showing various fragrance emission modes of the ornament according to the second embodiment of the present invention.

First, FIG. 7 shows a closed mode among the fragrance emission modes of the ornament according to the second embodiment of the present invention.

In the closed mode, the first coupling magnet 15a of the base 14 is coupled to the first sliding magnet 18a of the cover 17 by means of their magnetic force, and the second coupling magnet 15b of the base 14 is coupled to the second sliding magnet 18b of the cover 17 by means of their magnetic force. As a result, as shown, the accommodation recess 14a in which the fragrance cartridge 20 is built is not exposed to the outside by means of the cover 17 located on top of the base 14.

In the closed mode, accordingly, the fragrance cartridge 20 built in the accommodation recess 14a is not exposed directly to the outside, and fragrance emission is carried out only through a gap between the base 14 and the cover 17, so that the amount of fragrance emitted is extremely small.

The closed mode is selected and appropriately used in a personal space having no outside activities (for example, inside the house) or when he or she sleeps, and if the use time in the closed mode is long, the life span of the fragrance cartridge 20 can be extended.

In specific, only if the wearer's fingertip comes into contact with the cover 17 to slightly push the cover 17 in a horizontal direction, the cover 17 swings horizontally to allow the first coupling magnet 15a and the second coupling magnet 15b of the base 14 and the first sliding magnet 18a and the second sliding magnet 18b of the cover 17 to be moved in position and then coupled to each other by means of their magnetic force, so that the conversion into the closed mode can be performed easily and conveniently.

In this case, the cover 17 has a plurality of through holes formed thereon so as to allow a relatively large amount of fragrance to be emitted to the outside in the closed mode.

Figure 8:
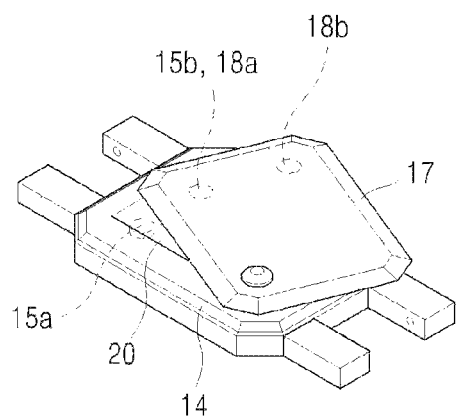

Next, FIG. 8 shows a wearer side quarter open mode among the fragrance emission modes of the ornament according to the second embodiment of the present invention.

In the wearer side quarter open mode, the second coupling magnet 15b of the base 14 is coupled to the first sliding magnet 18a of the cover 17 by means of their magnetic force, and the first coupling magnet 15a of the base 14 is not coupled to the second sliding magnet 18b of the cover 17. If the wearer's fingertip comes into contact with the cover 17 with respect to the body 10 that is in the closed mode to slightly push the cover 17 until the cover 17 horizontally swings (in a clockwise direction in the figure), the closed mode is converted into the wearer side quarter open mode. In the same manner as above, if the wearer's fingertip comes into contact with the cover 17 to slightly push the cover 17 in a counterclockwise direction, the wearer side quarter open mode can be converted into the closed mode.

If the closed mode is converted into the wearer side quarter open mode, the force applied to the cover 17 is a degree of force capable of just releasing the attractive force between the first coupling magnet 15a and the first sliding magnet 18a and the attractive force between the second coupling magnet 15b and the second sliding magnet 18b. In this case, if the attractive force between the first coupling magnet 15a and the first sliding magnet 18a and the attractive force between the second coupling magnet 15b and the second sliding magnet 18b are released through the application of the force in the horizontal swing direction (in the clockwise direction in the figure), the second coupling magnet 15b and the first sliding magnet 18a are naturally coupled to each other by means of their attractive force.

As a result, as shown, a portion (about ¼ of top surface) of the fragrance cartridge 20 built in the accommodation recess 14a is exposed to the wearer side by means of the cover 17 located on top of the base 14.

In the wearer side quarter open mode, accordingly, the fragrance cartridge 20 built in the accommodation recess 14a emits the fragrance through the open gap toward the wearer side.

In the wearer side quarter open mode, the wearer can send his or her desired fragrance to himself or herself, so that his or her mood can be improved through soft fragrance at a place where he or she does not take a lot of motions, and because the open portion of the fragrance cartridge 20 is small, the life span of the fragrance cartridge 20 can be extended.

In specific, only if the wearer's fingertip comes into contact with the horizontally swingable cover 17 to slightly push the cover 17 in a horizontal direction, the cover 17 swings horizontally to allow the first sliding magnet 18a of the cover 17 to be moved in position, so that the conversion into the wearer side quarter open mode can be performed easily and conveniently. Also, only a portion of the accommodation recess 14a is open by means of the cover 17, thereby advantageously preventing the fragrance cartridge 20 from escaping from the accommodation recess 14a.

Figure 9:
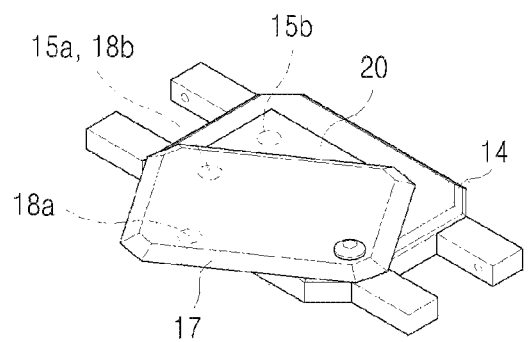

Next, FIG. 9 shows the other person side quarter open mode among the fragrance emission modes of the ornament according to the second embodiment of the present invention.

In the other person side quarter open mode, the first coupling magnet 15a of the base 14 is coupled to the second sliding magnet 18b of the cover 17 by means of their magnetic force, and the second coupling magnet 15b of the base 14 is not coupled to the first sliding magnet 18a of the cover 17. If the wearer's fingertip comes into contact with the cover 17 with respect to the body 10 that is in the closed mode to slightly push the cover 17 until the cover 17 horizontally swings (in the counterclockwise direction in the figure), the closed mode is converted into the other person side quarter open mode. In the same manner as above, if the wearer's fingertip comes into contact with the cover 17 to slightly push the cover 17 in the clockwise direction, the other person side quarter open mode can be converted into the closed mode.

If the closed mode is converted into the other person side quarter open mode, the force applied to the cover 17 is a degree of force capable of just releasing the attractive force between the first coupling magnet 15a and the first sliding magnet 18a and the attractive force between the second coupling magnet 15b and the second sliding magnet 18b. In this case, if the attractive force between the first coupling magnet 15a and the first sliding magnet 18a and the attractive force between the second coupling magnet 15b and the second sliding magnet 18b are released through the application of the force to the cover 17 in the horizontal swing direction (in the counterclockwise direction in the figure), the first coupling magnet 15a and the second sliding magnet 18b are naturally coupled to each other by means of their attractive force.

As a result, as shown, a portion (about ¼ of top surface) of the fragrance cartridge 20 built in the accommodation recess 14a is exposed to the other person side by means of the cover 17 located on top of the base 14.

In the other person side quarter open mode, accordingly, the fragrance cartridge 20 built in the accommodation recess 14a emits the fragrance through the open gap toward the other person side, not the wearer side.

In the other person side quarter open mode, the wearer can send his or her desired fragrance to the other person side, so that he or she can appeal his or her attraction through soft fragrance at a place where he or she does not take a lot of motions, and because the open portion of the fragrance cartridge 20 is small, the life span of the fragrance cartridge 20 can be extended.

In specific, only if the wearer's fingertip comes into contact with the horizontally swingable cover 17 to slightly push the cover 17 in a horizontal direction, the cover 17 swings horizontally to allow the second sliding magnet 18b of the cover 17 to be moved in position, so that the conversion into the other person side quarter open mode can be performed easily and conveniently. Also, only a portion of the accommodation recess 14a is open by means of the cover 17, thereby advantageously preventing the fragrance cartridge 20 from escaping from the accommodation recess 14a.

Figure 10:
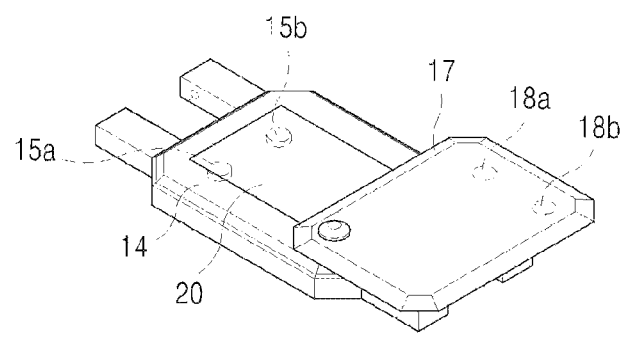

Next, FIG. 10 shows a half open mode among the fragrance emission modes of the ornament according to the second embodiment of the present invention.

In the half open mode, the first coupling magnet 15a and the second coupling magnet 15b of the base 14 are not coupled to the first sliding magnet 18a and the second sliding magnet 18b of the cover 17. If the wearer's fingertip comes into contact with the cover 17 with respect to the body 10 that is in the wearer side quarter open mode to slightly push the cover 17 until the cover 17 horizontally swings (in the clockwise direction in the figure), the wearer side quarter open mode is converted into the half open mode. In the same manner as above, if the wearer's fingertip comes into contact with the cover 17 to slightly push the cover 17 in the counterclockwise direction, the half open mode can be converted into the wearer side quarter open mode.

If the wearer side quarter open mode is converted into the half open mode, the force applied to the cover 17 is a degree of force capable of just releasing the attractive force between the second coupling magnet 15b and the first sliding magnet 18a that are in the wearer side quarter open mode.

As a result, as shown, half of the fragrance cartridge 20 built in the accommodation recess 14a is exposed to the outside by means of the cover 17 located on top of the base 14.

In the half open mode, accordingly, the fragrance cartridge 20 built in the accommodation recess 14a emits the fragrance through the open gap by half of the fragrance cartridge 20.

In the half open mode, the wearer can send his or her desired fragrance to himself or herself and the other person side, so that his or her mood can be improved through the fragrance, while he or she can appeal his or her attraction through the fragrance, at a place where he or she does not take a lot of motions, and because the open portion is half of the fragrance cartridge 20, the life span of the fragrance cartridge 20 can be extended.

In specific, only if the wearer's fingertip comes into contact with the horizontally swingable cover 17 to slightly push the cover 17 in a horizontal direction, the cover 17 swings horizontally to allow the first sliding magnet 18a of the cover 17 to be moved in position, so that the conversion into the half open mode can be performed easily and conveniently. Also, only half of the accommodation recess 14a is open by means of the cover 17, thereby advantageously preventing the fragrance cartridge 20 from escaping from the accommodation recess 14a.

Figure 11:
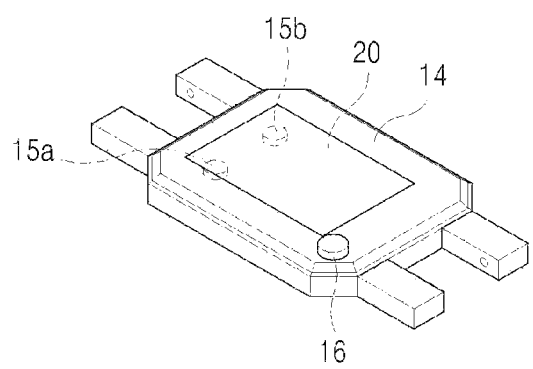

Next, FIG. 11 shows a full open mode among the fragrance emission modes of the ornament according to the second embodiment of the present invention.

In the full open mode, the hinge pin 16 is removed from the base 14 and the cover 17 to completely separate the cover 17 from the base 14. In the full open mode, the fragrance cartridge 20 built in the accommodation recess 14a is completely exposed to the outside so that it can be exchanged with new one or filled with the fragrance liquid.

In the full open mode, further, the fragrance cartridge 20 built in the accommodation recess 14a is completely open to the outside, thereby emitting a large amount of fragrance to the outside.

In the full open mode, the wearer can send his or her desired fragrance in large amount to himself or herself and the other person side, so that his or her mood can be improved through strong fragrance, while he or she can appeal his or her attraction through the strong fragrance, at a place where he or she does not take a lot of motions.

On the other hand, only if the wearer's fingertip comes into contact with the cover 17 to slightly push the cover 17 in the horizontal direction, the closed mode as shown in FIG. 7 can be converted into the wearer side quarter open mode as shown in FIG. 8 and into the other person side quarter open mode as shown in FIG. 9. In the same manner as above, if the wearer's fingertip comes into contact with the cover 17 to slightly push the cover 17, the wearer side quarter open mode and the other person side quarter open mode can be converted into the closed mode.

In this case, it is important to provide the parts capable of performing the mode conversion easily just through the wearer's slight finger motions at any time and place, without requiring any skill.

That is, it is needed to have the parts for easily and accurately performing the state conversion from the closed mode into the quarter open modes and for stably keeping the converted modes.

To do this, the ornament according to the present invention is configured to limit an arrangement structure among the hinge pin 16 for horizontally swinging the cover 17 and the coupling magnets 15a and 15b and the sliding magnets 18a and 18b for determining the operating radius of the cover 17 swung horizontally, so that it is possible to accurately perform the mode conversion and to stably keep the converted modes, irrespective of the free shapes of the body 10 and the magnets.

Figure 12:
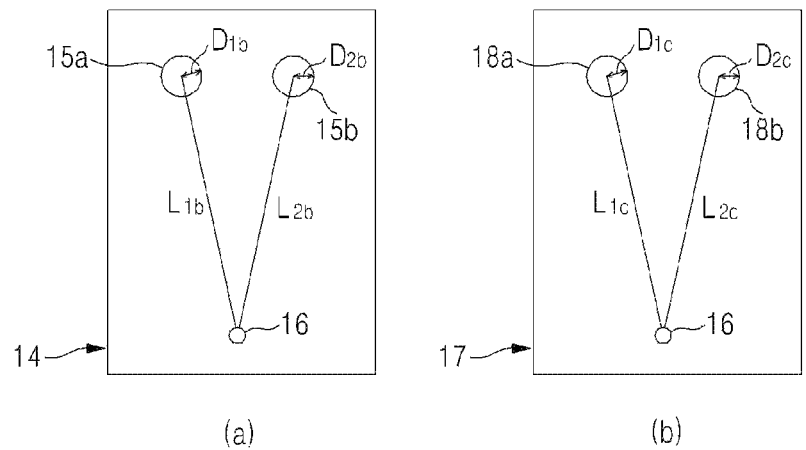
FIGS. 12 and 13 are views showing the limitations in the arrangements of coupling parts of the ornament according to the second embodiment of the present invention.

So as to explain the arrangement structure according to the present invention, FIG. 12A shows the top of the base 14 and FIG. 12B shows the underside of the cover 17. In this case, the top of the base 14 and the underside of the cover 17 are opposite to each other and are thus coupled to each other by means of the magnetic forces when the base 14 and the cover 17 constitute the body 10.

First, the hinge pin 16, the first coupling magnet 15a, and the second coupling magnet 15b are located on the top of the base 14.

In this case, as shown, it is assumed that a distance from the hinge pin 16 to the center of the first coupling magnet 15a is $L_{1b}$ and a distance from the hinge pin 16 to the center of the second coupling magnet 15b is $L_{2b}$. Further, it is assumed that an average distance from the center of the first coupling magnet 15a to the outermost periphery thereof is $D_{1b}$ and an average distance from the center of the second coupling magnet 15b to the outermost periphery thereof is $D_{2b}$.

In this case, the $D_{1b}$ and $D_{2b}$ are defined as the average distances from the centers of the magnets to the outermost peripheries thereof, and if the magnets have circular sections, as shown in FIGS. 12A and 12B, the $D_{1b}$ and $D_{2b}$ are the radiuses of the magnets. According to the present invention, however, the first coupling magnet 15a and the second coupling magnet 15b are not limited to the circular shapes. That is, they may have polygonal sections like triangular or square sections, undefined sections, or the like. If they have polygonal or undefined sections, the distances from the centers of the magnets to the outermost peripheries thereof are determined upon the positions of the outermost peripheries of the magnets, and accordingly, the ornament according to the present invention includes the magnets free in shape having the $D_{1b}$ and $D_{2b}$ defined as the average distances from the centers thereof to various outermost peripheries thereof.

Next, the hinge pin 16, the first sliding magnet 18a, and the second sliding magnet 18b are located on the underside of the cover 17.

In this case, as shown, it is assumed that a distance from the hinge pin 16 to the center of the first sliding magnet 18a is $L_{1c}$ and a distance from the hinge pin 16 to the center of the second sliding magnet 18b is $L_{2c}$. Further, it is assumed that an average distance from the center of the first sliding magnet 18a to the outermost periphery thereof is $D_{1c}$ and an average distance from the center of the second sliding magnet 18b to the outermost periphery thereof is $D_{2c}$.

Like this, the arrangement of the parts, in which the conversion from the closed mode into the wearer side quarter open mode can be performed easily and accurately and the converted mode can be stably kept, has to satisfy the following Mathematical equation 1.

$$L_{2b} - D_{2b} \le L_{1c} \le L_{2b} + D_{2b}$$ [Mathematical equation 1]

If the parts are arranged to satisfy Mathematical equation 1, the wearer's fingertip comes into contact with the cover 17 to slightly push the cover 17 in a horizontal direction with respect to the body 10 that is in the closed mode, and accordingly, the cover 17 swings horizontally (in the clockwise direction in FIG. 8) to allow the attractive force between the first coupling magnet 15a and the first sliding magnet 18a and the attractive force between the second coupling magnet 15b and the second sliding magnet 18b to be released from the closed mode. Simultaneously, the second coupling magnet 15b and the first sliding magnet 18a, which are located in the swinging direction, are naturally coupled to each other by means of their magnetic force.

If the closed mode is converted into the wearer side quarter open mode, the force applied to the cover 17 is a degree of force capable of just releasing the attractive force between the first coupling magnet 15a and the first sliding magnet 18a and the attractive force between the second coupling magnet 15b and the second sliding magnet 18b. In this case, the wearer side quarter open mode is made by means of the natural attractive force between the second coupling magnet 15b and the first sliding magnet 18a. Through the limitation in the arrangement of the parts under Mathematical equation 1, in specific, the coupling state between the second coupling magnet 15b and the first sliding magnet 18a can be stably maintained by means of their attractive force generated when they face each other at a given area capable of keeping their coupling state.

If the parts are arranged to satisfy Mathematical equation 1, the conversion from the closed mode into the wearer side quarter open mode can be performed easily, accurately, and stably, irrespective of the plane size of the base 14 or the cover 17, the position of the hinge pin 16, and the positions of the magnets. Further, the ornament product can be made, irrespective of the sizes or shapes of the magnets.

Next, the arrangement of the parts, in which the conversion from the closed mode into the other person side quarter open mode can be performed easily and accurately and the converted mode can be stably kept, has to satisfy the following Mathematical equation 2.

$$L_{1b} \le D_{1b} \le L_{2b} \le L_{1b} + D_{1b}$$ [Mathematical equation 2]

If the parts are arranged to satisfy Mathematical equation 2, the wearer's fingertip comes into contact with the cover 17 to slightly push the cover 17 in a horizontal direction with respect to the body 10 that is in the closed mode, and accordingly, the cover 17 swings horizontally (in the counterclockwise direction in FIG. 9) to allow the attractive force between the first coupling magnet 15a and the first sliding magnet 18a and the attractive force between the second coupling magnet 15b and the second sliding magnet 18b to be released from the closed mode. Simultaneously, the first coupling magnet 15a and the second sliding magnet 18b, which are located in the swinging direction, are naturally coupled to each other by means of their magnetic force.

If the closed mode is converted into the other person side quarter open mode, the force applied to the cover 17 is a degree of force capable of just releasing the attractive force between the first coupling magnet 15a and the first sliding magnet 18a and the attractive force between the second coupling magnet 15b and the second sliding magnet 18b. In this case, the other person side quarter open mode is made by means of the natural attractive force between the first coupling magnet 15a and the second sliding magnet 18b. Through the limitation in the arrangement of the parts under Mathematical equation 2, in specific, the coupling state between the first coupling magnet 15a and the second sliding magnet 18b can be stably maintained by means of their attractive force generated when they face each other at a given area capable of keeping their coupling state.

If the parts are arranged to satisfy Mathematical equation 2, the conversion from the closed mode into the other person side quarter open mode can be performed easily, accurately, and stably, irrespective of the plane size of the base 14 or the cover 17, the position of the hinge pin 16, and the positions of the magnets. Further, the ornament product can be made, irrespective of the sizes or shapes of the magnets.

In addition, if the parts are arranged to satisfy both of Mathematical equation 1 and Mathematical equation 2, the conversion into the wearer side quarter open mode and the other person side quarter open mode can be performed easily and stably on the single product.

On the other hand, as described above, if the cover 17 rotates in a given direction, the conversion from the closed mode into the wearer side quarter open mode or the other person side quarter open mode can be performed gently through the magnetic coupling and the limited arrangement structures (Mathematical equation 1 and Mathematical equation 2) of the coupled parts.

In this case, on one product, generally, both of the conversion from the closed mode into the wearer side quarter open mode, which satisfies Mathematical equation 1, and the conversion from the closed mode into the other person side quarter open mode, which satisfies Mathematical equation 2, can be carried out according to the characteristics of the product. However, if there is a need to diversify functions or price portfolios of the product or if it is desired to satisfy various control preferences of wearers, only one of the two conversion modes can be applied to the product, thereby launching the product limited in function.

In specific, if only one of the two conversion modes can be applied to the product, no magnetic coupling occurs in the rotation in the opposite direction to the rotating direction of the cover 17 in which the corresponding conversion mode is made, and accordingly, the cover 17 idles. As a result, a customized product to the wearer's mode preference in the use of fragrance can be made.

Figure 13:
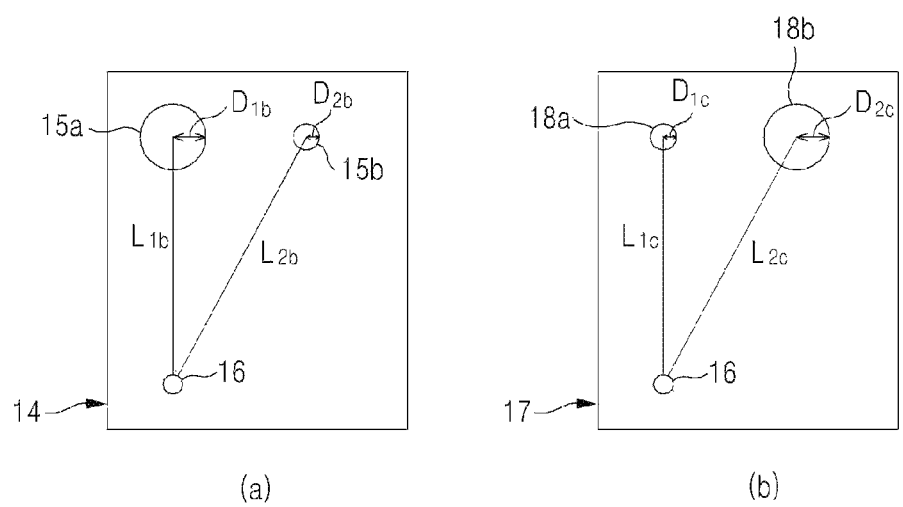

So as to explain the arrangement structure for the customized product limited in function, FIG. 13A shows the top of the base 14 and FIG. 13B shows the underside of the cover 17.

In this case, the sizes of the first coupling magnet 15a and the second coupling magnet 15b located on the top of the base 14 are different from each other. Further, the sizes of the first sliding magnet 18a and the second sliding magnet 18b located on the underside of the cover 17 are different from each other.

Further, the hinge pin 16 as the rotating shaft of the cover 17, which is located on the opposite side to the magnets, is positioned on the side surface of the accommodation recess 14a, not on the center thereof.

Like this, the arrangement of the parts, in which the conversion (Mathematical equation 1) from the closed mode into the wearer side quarter open mode is performed through the rotation of the cover 17 in a given direction and simultaneously, no magnetic coupling occurs in the rotation of the cover 17 in the opposite direction thereto to cause the cover 17 to idle, has to satisfy the following Mathematical equation 3.

$$|L_{1c}-L_{2b}|>D_{1c}+D_{2b} \quad \text{[Mathematical equation 3]}$$

In Mathematical equation 3, the $|L_{1c}-L_{2b}|$ indicates an absolute value of $L_{1c}-L_{2b}$.

If the parts are arranged to satisfy both of Mathematical equation 1 and Mathematical equation 3, the wearer's fingertip comes into contact with the cover 17 to slightly push the cover 17 in a horizontal direction with respect to the body 10 that is in the closed mode, and accordingly, the cover 17 swings horizontally (in the clockwise direction in FIG. 8) to allow the attractive force between the first coupling magnet 15a and the first sliding magnet 18a and the attractive force between the second coupling magnet 15b and the second sliding magnet 18b to be released from the closed mode. Simultaneously, the second coupling magnet 15b and the first sliding magnet 18a, which are located in the swinging direction, are naturally coupled to each other by means of their magnetic force, thereby converting the closed mode into the wearer side quarter open mode. Contrarily, if the wearer pushes the cover 17 to rotate the cover 17 in the opposite direction to the wearer side quarter open mode with respect to the body 10 that is in the closed mode, the attractive force between the first coupling magnet 15a and the first sliding magnet 18a and the attractive force between the second coupling magnet 15b and the second sliding magnet 18b are released from the closed mode by means of the pushing force. Simultaneously, the first coupling magnet 15a and the second sliding magnet 18b do not come into contact with each other during the rotation, thereby having no magnetic coupling therebetween. Accordingly, no magnetic coupling occurs in the corresponding direction to cause the cover 17 to idle.

As a result, the customized product limited in function can be made, so that the conversion into the wearer side quarter open mode when the cover 17 rotates in one direction is performed and the cover 17 idles when it rotates in the opposite direction to one direction.

Further, the arrangement of the parts, in which the conversion (Mathematical equation 2) from the closed mode into the other person side quarter open mode is performed through the rotation of the cover 17 in a given direction and simultaneously, no magnetic coupling occurs in the rotation of the cover 17 in the opposite direction thereto to cause the cover 17 to idle, has to satisfy the following Mathematical equation 4.

$$|L_{2c}-L_{1b}|>D_{2c}+D_{1b} \quad \text{[Mathematical equation 4]}$$

In Mathematical equation 4, the $|L_{2c}-L_{1b}|$ indicates an absolute value of $L_{2c}-L_{1b}$.

If the parts are arranged to satisfy both of Mathematical equation 2 and Mathematical equation 4, the wearer's fingertip comes into contact with the cover 17 to slightly push the cover 17 in a horizontal direction with respect to the body 10 that is in the closed mode, and accordingly, the cover 17 swings horizontally (in the counterclockwise direction in FIG. 9) to allow the attractive force between the first coupling magnet 15a and the first sliding magnet 18a and the attractive force between the second coupling magnet 15b and the second sliding magnet 18b to be released from the closed mode. Simultaneously, the first coupling magnet 15a and the second sliding magnet 18b, which are located in the swinging direction, are naturally coupled to each other by means of their magnetic force, thereby converting the closed mode into the other person side quarter open mode. Contrarily, if the wearer pushes the cover 17 to rotate the cover 17 in the opposite direction to the other person side quarter open mode with respect to the body 10 that is in the closed mode, the attractive force between the first coupling magnet 15a and the first sliding magnet 18a and the attractive force between the second coupling magnet 15b and the second sliding magnet 18b are released from the closed mode by means of the pushing force. Simultaneously, the second coupling magnet 15b and the first sliding magnet 18a do not come into contact with each other during the rotation, thereby having no magnetic coupling therebetween. Accordingly, no magnetic coupling occurs in the corresponding direction to cause the cover 17 to idle.

As a result, the customized product limited in function can be made so that the conversion into the other person side quarter open mode when the cover 17 rotates in one direction is made and the cover 17 idles when it rotates in the other direction.

On the other hand, as described above, the body 10 constituting the ornament according to the present invention may have various shapes. For example, the body 10 is a main ornamental part for various ornaments such as a bracelet, pendant, ring, earring, necklace, anklet, brooch, hair band, hair pin, medal, clip, and so on, and otherwise, the body 10 is an auxiliary ornamental part like a connector adapted to allow the ornament to be worn on the human body.

Among them, if the body 10 has the shape of the main ornamental part constituting the bracelet, the body 10 is kept in direct contact with the wearer's wrist when it is worn on the wearer's wrist and thus receives the wearer's body temperature.

According to the present invention, after the raw fragrance liquid is put in the accommodation recess 14a in which the fragrance cartridge 20 is built, the fragrance cartridge 20 is submerged into the raw fragrance liquid for given time, and otherwise, the raw fragrance liquid is directly sprayed or applied to the fragrance cartridge 20 and is thus contained in the pores of the fragrance cartridge 20.

The raw fragrance liquid enters the pores of the fragrance cartridge 20 and is thus filled therein, and accordingly, the filled state is kept by means of the surface tension in the pores of the fragrance cartridge 20. Next, the surface of the raw fragrance liquid absorbs heat energy to vaporize the molecules having high energy, thereby emitting the fragrance around the fragrance cartridge 20.

In specific, the factor that has the greatest influence on the vaporization of the raw fragrance liquid, that is, the surface tension is the temperature of the raw fragrance liquid. As the surrounding temperature becomes high, the surface tension becomes reduced, so that a relatively large amount of fragrance is emitted around the fragrance cartridge 20.

As the temperature of the body 10 with the fragrance cartridge 20 built therein becomes high, an amount of fragrance emitted from the fragrance cartridge 20 becomes large, and contrarily, as the temperature of the body 10 with the fragrance cartridge 20 built therein becomes low, an amount of fragrance emitted from the fragrance cartridge 20 becomes small.

Under the above-mentioned principle, the inventor has studied for a long time the optimized structure with the body 10 and the fragrance cartridge 20, so that a relatively large amount of fragrance can be emitted by receiving the wearer's body temperature when the ornament like a bracelet is worn on the wearer's wrist and a relatively small amount of fragrance can be emitted from the ornament when the ornament is just kept in a given place, without being worn on the wearer's wrist.

Figure 14:
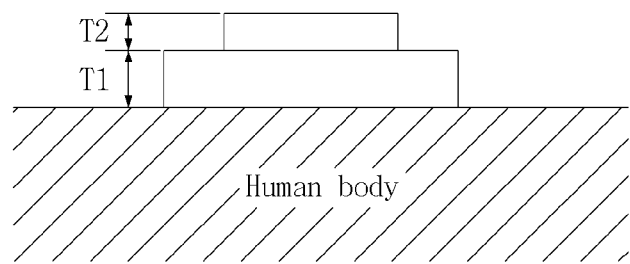
FIG. 14 is a sectional view showing a relation between the body of the ornament according to the present invention and the human body.

FIG. 14 is a sectional view showing a relation between the body of the ornament according to the present invention and the human body.

First, the body 10 is made by uniformly mixing a raw ceramic material, filling the mixed ceramic material in a mold, and sintering the filled ceramic material at a high temperature. Accordingly, the body 10 is a non-porous part with no pores, and the contact wall 11 as a portion of the body 10, which comes into direct contact with the human body, is a non-porous part.

Also, the fragrance cartridge 20 is made by filling a ceramic material in a mold, pressurizing the filled material under a given pressure to make pores thereon, and sintering the molded material at a high temperature. Accordingly, the fragrance cartridge 20 is porous, and the pores of the fragrance cartridge 20 contain the fragrance emitting substance.

In this case, there is a difference in the thermal conductivity between the non-porous ceramic and the porous ceramic. Basically, the non-porous ceramic made of zirconia has the thermal conductivity of about 30 W/m·k, and the porous ceramic made of zirconia has the thermal conductivity of about 40 to 50 W/m·k.

It is important that the non-porous contact wall 11 directly receiving the wearer's body temperature and the porous fragrance cartridge 20 facing the contact wall 11 and containing the raw fragrance liquid serve to supply heat energy to the surface of the raw fragrance liquid by means of the wearer's body temperature, thereby emitting a relatively large amount of fragrance. If the contact wall 11 and the fragrance cartridge 20 do not receive the wearer's body temperature, on the other hand, a relatively small amount of fragrance is emitted.

In this case, the porous fragrance cartridge 20 is adjusted in molding pressure when molded by means of a press, so that it has pore sizes of 10 to 200 µm and porosity of 10 to 70%. In this case, the entire size of the fragrance cartridge 20 having such porous sizes and porosity has a direct relation to the moisture content of the raw fragrance liquid. That is, if the size of the fragrance cartridge 20 is large, a relatively large amount of raw fragrance liquid is contained in the fragrance cartridge 20, and contrarily, if the size of the fragrance cartridge 20 is small, a relatively small amount of raw fragrance liquid is contained in the fragrance cartridge 20. However, if the size of the fragrance cartridge 20 is large, the size of the body 10 accommodating the fragrance cartridge 20 therein and the sizes of the straps 30 may become large, thereby increasing the weight of the bracelet to cause the productivity of the bracelet product for women to become deteriorated. In this case, the non-porous body 10 has the pore sizes and porosity less than those of the porous fragrance cartridge 20.

If it is desired to allow the bracelet for women to be worn on a woman having a thin wrist, generally, the head as the body 10 has a plane size of 20×20 mm and a weight of 20 to 50 g. That is, the plane size of the body 10 in which the fragrance cartridge 20 is built is somewhat limited.

Accordingly, the thickness T2 of the fragrance cartridge 20 and the thickness T1 of the contact wall 11 located on the underside of the body 10 are optimized to thus emit the fragrance for a day or more, and simultaneously, the fragrance cartridge 20 and the contact wall 11 receive the wearer's body temperature to automatically adjust the amount of fragrance emitted according to whether the bracelet is worn or not.

Figure 15:
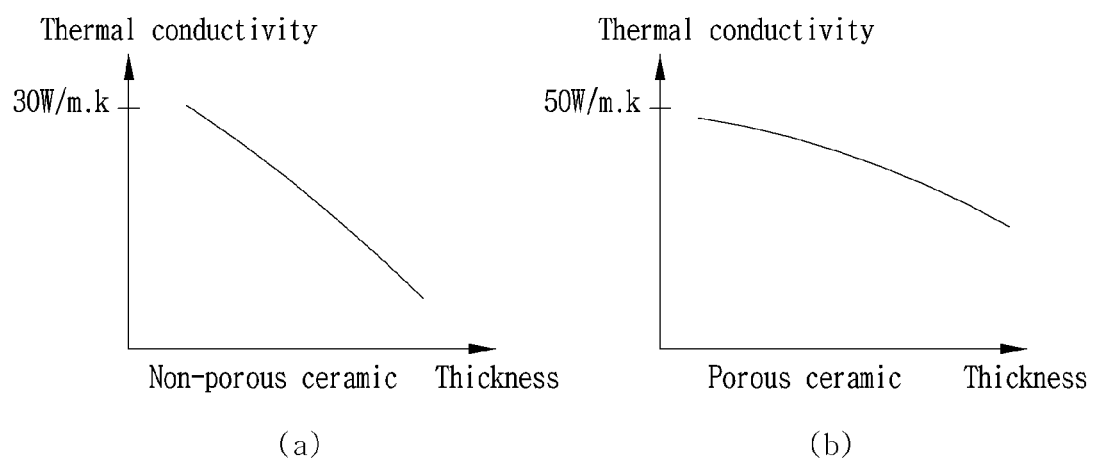
FIGS. 15 and 16 are graphs showing relations between the thicknesses of the body and the fragrance cartridge and the fragrance emission forces in the ornament according to the present invention.

FIGS. 15A and 15B are graphs showing the thermal conductivity between the non-porous ceramic (See FIG. 15A) and the porous ceramic (See FIG. 15B) according to their thicknesses at a reference temperature (20° C.). As the thicknesses of the non-porous ceramic and the porous ceramic become high, the amount of heat passing through the unit sectional areas of the non-porous ceramic and the porous ceramic is small, so that the thermal conductivity of the non-porous ceramic and the porous ceramic becomes drastically lowered.

Figure 16:
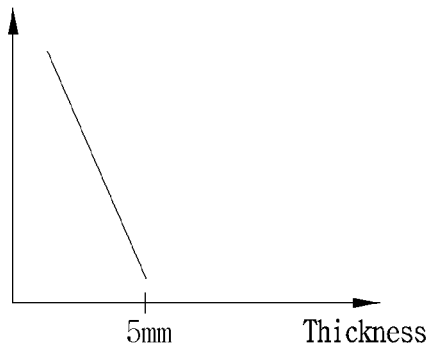
Figure 16:
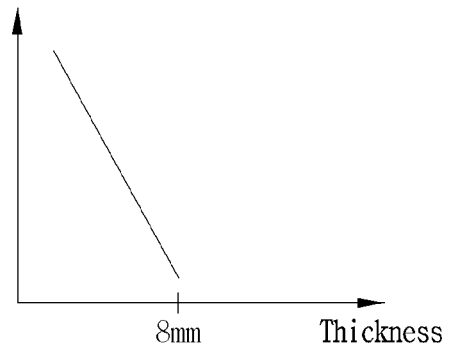

FIGS. 16A and 16B are graphs showing the results of pre-tests for the transmissibility of the body temperature (36.5° C.) between the non-porous ceramic (See FIG. 16A) and the porous ceramic (See FIG. 156) according to their thicknesses. In the pre-tests, as each ceramic having a sectional size of 20×20 mm is increased in thickness by a unit of 0.5 mm, a temperature equal to the body temperature is transferred to one surface of the ceramic, and a temperature transferred through the other side surface thereof is measured. According to the pre-test results, as the thicknesses of all of the non-porous ceramic and the porous ceramic become high, the transmissibility of the body temperature becomes drastically lowered. In specific, if the thickness of the non-porous ceramic is greater than 5 mm, the body temperature is not transferred at all, and if the thickness of the porous ceramic is greater than 8 mm, the body temperature is not transferred at all.

In this case, it is important that under the structure of the ornament according to the present invention, the porous fragrance cartridge 20 containing the raw fragrance liquid is located to face the non-porous contact wall 11 directly receiving the body temperature.

In main tests, accordingly, a non-porous ceramic having a sectional size of 20×20 cm is located as the corresponding part to the contact wall 11, and a porous ceramic having a sectional size of 12×12 cm is located as the corresponding part to the fragrance cartridge 20 in such a manner as to face the non-porous ceramic. Next, the temperature like the body temperature is transferred to the outer surface of the non-porous ceramic, and the temperature transferred to the fragrance cartridge 20 is measured. In this case, the thickness of the non-porous ceramic is increased by 0.2 mm from its minimum thickness of 1.5 mm, and the thickness of the porous ceramic is increased by 0.2 mm from its minimum thickness of 0.5 mm. Further, the duration time of the fragrance emitted is measured according to the thicknesses of the porous ceramic.

The test results are suggested in the following Table 1. The porous ceramic used in the tests has pore sizes of 100 μm and porosity of 50%.

TABLE 1

| Test No. | Contact temperature (° C.) | Thickness of non-porous ceramic(mm) | Thickness of porous ceramic(mm) | Temperature of porous ceramic(° C.) | Fragrance duration time (hour) |
|---|---|---|---|---|---|
| 1-1 | 36.5 | 1.5 | 0.5 | 30 | 8 |
| 1-2 | 36.5 | 1.5 | 0.7 | 29 | 9 |
| 1-3 | 36.5 | 1.5 | 0.9 | 29 | 10 |
| 1-4 | 36.5 | 1.5 | 1.1 | 29 | 12 |
| 1-5 | 36.5 | 1.5 | 1.3 | 28 | 12 |
| 2-1 | 36.5 | 1.7 | 0.5 | 30 | 9 |
| 2-2 | 36.5 | 1.7 | 0.7 | 30 | 9 |
| 2-3 | 36.5 | 1.7 | 0.9 | 30 | 10 |
| 2-4 | 36.5 | 1.7 | 1.1 | 29 | 11 |
| 2-5 | 36.5 | 1.7 | 1.3 | 27 | 12 |
| 3-1 | 36.5 | 1.9 | 0.5 | 29 | 11 |
| 3-2 | 36.5 | 1.9 | 0.7 | 28 | 10 |
| 3-3 | 36.5 | 1.9 | 0.9 | 28 | 12 |
| 3-4 | 36.5 | 1.9 | 1.1 | 37 | 12 |
| 3-5 | 36.5 | 1.9 | 1.3 | 25 | 14 |
| 4-1 | 36.5 | 2.1 | 0.5 | 30 | 10 |
| 4-2 | 36.5 | 2.1 | 0.7 | 30 | 10 |
| 4-3 | 36.5 | 2.1 | 0.9 | 30 | 10 |
| 4-4 | 36.5 | 2.1 | 1.1 | 29 | 12 |
| 4-5 | 36.5 | 2.1 | 1.3 | 27 | 16 |
| 5-1 | 36.5 | 2.3 | 0.5 | 30 | 10 |
| 5-2 | 36.5 | 2.3 | 0.7 | 30 | 11 |
| 5-3 | 36.5 | 2.3 | 0.9 | 29 | 11 |
| 5-4 | 36.5 | 2.3 | 1.1 | 29 | 13 |
| 5-5 | 36.5 | 2.3 | 1.3 | 28 | 16 |
| 6-1 | 36.5 | 2.5 | 0.5 | 30 | 17 |
| 6-2 | 36.5 | 2.5 | 0.7 | 30 | 19 |
| 6-3 | 36.5 | 2.5 | 0.9 | 30 | 24 |
| 6-4 | 36.5 | 2.5 | 1.1 | 30 | 27 |
| 6-5 | 36.5 | 2.5 | 1.3 | 27 | 30 |
| 7-1 | 36.5 | 2.7 | 0.5 | 30 | 18 |
| 7-2 | 36.5 | 2.7 | 0.7 | 30 | 19 |
| 7-3 | 36.5 | 2.7 | 0.9 | 29 | 24 |
| 7-4 | 36.5 | 2.7 | 1.1 | 30 | 28 |
| 7-5 | 36.5 | 2.7 | 1.3 | 28 | 31 |
| 8-1 | 36.5 | 2.9 | 0.5 | 17 | 24 |
| 8-2 | 36.5 | 2.9 | 0.7 | 17 | 26 |
| 8-3 | 36.5 | 2.7 | 0.9 | 15 | 26 |
| 8-4 | 36.5 | 2.7 | 1.1 | 15 | 29 |
| 8-5 | 36.5 | 2.7 | 1.3 | 15 | 33 |

As appreciated from Table 1, as the thickness of the non-porous ceramic becomes high, the thermal conductivity of the combination of the non-porous ceramic and the porous ceramic becomes slowly lowered. Further, as the thickness of the porous ceramic becomes high, the size of the ceramic becomes large to increase the moisture content of the raw fragrance liquid, so that the duration time of the fragrance emitted can be extended.

As the thickness of the porous ceramic becomes high, while the non-porous ceramic is the same in thickness, the thermal conductivity of the combination of the non-porous ceramic and the porous ceramic becomes slowly lowered.

A purpose of the main tests is to find the optimized thicknesses of the contact wall 11 and the fragrance cartridge 20 that are capable of transferring the body temperature to the porous fragrance cartridge 20 well, while having the standard plane sizes, thereby naturally emitting a relatively large amount of fragrance when the bracelet is worn on the wearer.

In case of the test Nos. 1 to 5, the thickness of the non-porous ceramic is relatively low, so that the transmissibility of the body temperature to the porous ceramic is very high, thereby automatically adjusting the amount of fragrance according to whether the bracelet is worn or not, but the porous ceramic containing the raw fragrance liquid limitedly therein cannot emit the fragrance over 24 hours due to a relatively high temperature, so that it is difficult to produce the bracelet as a product.

In case of the test Nos. 6 and 7, contrarily, the thickness of the non-porous ceramic is appropriate, so that the transmissibility of the body temperature to the porous ceramic is high, thereby automatically adjusting the amount of fragrance according to whether the bracelet is worn or not, and the porous ceramic containing the raw fragrance liquid limitedly therein can emit the fragrance over 24 hours through an appropriate temperature, so that it is desirable to produce the bracelet as a product.

In case of the test No. 8, the thickness of the non-porous ceramic is relatively high, so that the transmissibility of the body temperature to the porous ceramic is very low, thereby making it impossible to automatically adjust the amount of fragrance according to whether the bracelet is worn or not. Accordingly, the porous ceramic containing the raw fragrance liquid limitedly therein can emit the fragrance over 24 hours through an appropriate temperature, but it is difficult to produce the bracelet as a product.

According to the tests, it can be appreciated that when the contact wall 11 as the non-porous ceramic has a thickness of 1.5 to 2.0 mm and the fragrance cartridge 20 as the porous ceramic has a thickness of 0.5 to 1.3 mm and when the contact wall 11 as the non-porous ceramic has a thickness of 2.5 to 2.7 mm and the fragrance cartridge 20 as the porous ceramic has a thickness of 0.9 to 1.3 mm, the automatic adjustment in the amount of fragrance emitted and the excellent duration time of the fragrance are most desirably obtained.

The invention claimed is:

1. An ornament comprising:
    a body having an accommodation space formed therein; and
    a fragrance cartridge accommodatedly located in the accommodation space of the body and having internal pores adapted to contain a raw fragrance liquid therein,
    wherein the body and the fragrance cartridge are made of a ceramic material, and
    wherein the body comprises:
    a base adapted to accommodate the fragrance cartridge therein in such a manner as to allow one surface of the fragrance cartridge to be exposed to the outside; and
    a cover adapted to cover one surface of the base in such a manner as to allow an open state thereof to be changed by a wearer's finger motion.

2. The ornament according to claim 1, wherein the body has the shape of a main ornamental part of any one selected from various ornaments such as a bracelet, pendant, ring, earring, necklace, anklet, brooch, hair band, hair pin, medal, clip, and so on, and otherwise, the body has the shape of an auxiliary ornamental part adapted to allow the main ornamental part to be worn on the human body.

3. The ornament according to claim 1, wherein the body has any one of zirconia ($ZrO_2$) and alumina ($Al_2O_3$) as a main material so that the body becomes the ceramic material.

4. The ornament according to claim 1, wherein the fragrance cartridge has any one of zirconia and alumina as a main material so that the fragrance cartridge becomes porous ceramic.

5. The ornament according to claim 4, wherein the fragrance cartridge is submerged into the raw fragrance liquid or is sprayed or coated with the raw fragrance liquid so as to contain the raw fragrance liquid in the internal pores thereof.

6. The ornament according to claim 1, wherein the base comprises:
an accommodation recess formed in the middle portion of top surface thereof to accommodate the fragrance cartridge thereinto;
a hinge pin located on one side of top surface thereof around the accommodation recess; and
a first coupling magnet and a second coupling magnet located on the bottom of the accommodation recess, and
the cover comprises a first sliding magnet and a second sliding magnet located on the corresponding positions facing the first coupling magnet and the second coupling magnet of the base,
whereby the base and the cover are coupled to each other by the hinge pin to allow the cover to horizontally swing on the base.

7. The ornament according to claim 6, wherein the first coupling magnet and the second coupling magnet of the base have the same polarities as each other, and the first sliding magnet and the second sliding magnet of the cover have the opposite polarities to the first coupling magnet and the second coupling magnet of the base.

8. The ornament according to claim 7, wherein the first coupling magnet of the base is coupled to the first sliding magnet of the cover by magnetic forces thereof, and the second coupling magnet of the base is coupled to the second sliding magnet of the cover by magnetic forces thereof, so that the body emits fragrance in a closed mode with no exposure of the accommodation recess having the fragrance cartridge built therein to the outside.

9. The ornament according to claim 8, wherein if the cover is pushed by the wearer and horizontally swings around the hinge pin, the first sliding magnet of the cover is moved in position and is thus coupled to the second coupling magnet of the base by the magnetic forces, with no coupling between the first coupling magnet of the base and the second sliding magnet of the cover, so that the body emits the fragrance in a wearer side quarter open mode in which a portion of the fragrance cartridge is exposed to the wearer side.

10. The ornament according to claim 9, wherein a given arrangement is made to satisfy the following Mathematical equation so that the conversion into the wearer side quarter open mode is performed, $$L_{2b}-D_{2b} \leq L_{1c} \leq L_{2b}+D_{2b} \quad \text{[Mathematical equation]}$$

wherein the $L_{1c}$ indicates a distance from the hinge pin to the center of the first sliding magnet, the $L_{2b}$ indicates a distance from the hinge pin to the center of the second coupling magnet, and the $D_{2b}$ indicates an average distance from the center of the second coupling magnet to the outermost periphery thereof.

11. The ornament according to claim 10, wherein a given arrangement is made to satisfy the following Mathematical equation so that the conversion into the wearer side quarter open mode is performed according to the rotation of the cover in one direction, $$|L_{1c}-L_{2b}|>D_{1c}+D_{2b} \quad \text{[Mathematical equation]}$$

wherein the $D_{1c}$ indicates an average distance from the center of the second sliding magnet to the outermost periphery thereof, and the $|L_{1c}-L_{2b}|$ indicates an absolute value of $L_{1c}-L_{2b}$.

12. The ornament according to claim 8, wherein if the cover is pushed by the wearer and horizontally swings around the hinge pin, the second sliding magnet of the cover is moved in position and is thus coupled to the first coupling magnet of the base by the magnetic forces, with no coupling between the second coupling magnet of the base and the first sliding magnet of the cover, so that the body emits the fragrance in the other person side quarter open mode in which a portion of the fragrance cartridge is exposed to the other person side.

13. The ornament according to claim 12, wherein a given arrangement is made to satisfy the following Mathematical equation so that the conversion into the other person side quarter open mode is performed, $$L_{1b}-D_{1b} \leq L_{2c} \leq L_{1b}+D_{1b} \quad \text{[Mathematical equation]}$$

wherein the $L_{2c}$ indicates a distance from the hinge pin to the center of the second sliding magnet, the $L_{1b}$ indicates a distance from the hinge pin to the center of the first coupling magnet, and the $D_{1b}$ indicates an average distance from the center of the first coupling magnet to the outermost periphery thereof.

14. The ornament according to claim 13, wherein a given arrangement is made to satisfy the following Mathematical equation so that the conversion into the other person side quarter open mode is performed according to the rotation of the cover in one direction, while the cover is idling according to the rotation in the opposite direction to one direction, $$|L_{2c}-L_{1b}|>D_{2c}+D_{1b} \quad \text{[Mathematical equation]}$$

wherein the $D_{2c}$ indicates an average distance from the center of the second sliding magnet to the outermost periphery thereof, and the $|L_{2c}-L_{1b}|$ indicates an absolute value of $L_{2c}-L_{1b}$.

15. The ornament according to claim 8, wherein if the cover is pushed by the wearer and horizontally swings around the hinge pin, no coupling occurs between the first coupling magnet and the second coupling magnet of the base and the first sliding magnet and the second sliding magnet of the cover, so that the body emits the fragrance in a half open mode in which a portion of the fragrance cartridge is exposed to the other person side.

16. The ornament according to claim 7, wherein if the hinge pin is removed from the base and the cover to separate the cover from the base, the body emits the fragrance in a full open mode in which the fragrance cartridge is fully exposed to the outside.

17. An ornament comprising:
a body having an accommodation space formed therein and a contact wall located on the underside thereof to constitute the accommodation space, the contact wall coming into contact with the human body; and
a fragrance cartridge accommodatedly located in the accommodation space of the body in such a manner as to face the contact wall,
wherein the contact wall is made of a non-porous ceramic material, has a thickness of 1.5 to 2.9 mm, and the fragrance cartridge is made of a porous ceramic material, has a thickness of 0.5 to 1.3 mm, contains a raw fragrance liquid in internal pores thereof, and receives the body temperature of a wearer coming into direct contact with the contact wall to emit the fragrance contained therein.

18. The ornament according to claim 17, wherein the body and the fragrance cartridge have any one of zirconia ($ZrO_2$) and alumina ($Al_2O_3$) as a main material so that the body and the fragrance cartridge become the ceramic material.

19. The ornament according to claim 17, wherein the fragrance cartridge is submerged into the raw fragrance liquid or is sprayed or coated with the raw fragrance liquid so as to contain the raw fragrance liquid in the internal pores thereof.

20. The ornament according to claim 17, wherein the body and the fragrance cartridge have zirconia as a main material so that the body and the fragrance cartridge become the ceramic material, the fragrance cartridge has the internal pore sizes of 10 to 200 μm and porosity of 10 to 70%, the contact wall has a thickness of 2.5 to 2.7 mm, and the fragrance cartridge has a thickness of 0.9 to 1.3 mm, so that the fragrance is emitted over a day and the amount of fragrance emitted is automatically adjusted according to whether the ornament is worn.

\* \* \* \* \*